(12) United States Patent
Milliman

(10) Patent No.: US 11,484,316 B2
(45) Date of Patent: *Nov. 1, 2022

(54) CIRCULAR STAPLING DEVICE INCLUDING BUTTRESS MATERIAL

(71) Applicant: Covidien LP, Mansfield, MA (US)

(72) Inventor: Keith Milliman, Port Richey, FL (US)

(73) Assignee: COVIDIEN LP, Mansfield, MA (US)

( * ) Notice: Subject to any disclaimer, the term of this patent is extended or adjusted under 35 U.S.C. 154(b) by 281 days.

This patent is subject to a terminal disclaimer.

(21) Appl. No.: 16/785,378

(22) Filed: Feb. 7, 2020

(65) Prior Publication Data
US 2020/0170642 A1 Jun. 4, 2020

Related U.S. Application Data

(63) Continuation of application No. 15/875,419, filed on Jan. 19, 2018, now Pat. No. 10,595,872, which is a
(Continued)

(51) Int. Cl.
*A61B 17/072* (2006.01)
*A61B 17/115* (2006.01)
(Continued)

(52) U.S. Cl.
CPC ........ *A61B 17/1155* (2013.01); *A61B 17/068* (2013.01); *A61B 17/0682* (2013.01);
(Continued)

(58) Field of Classification Search
CPC .............. A61B 17/1155; A61B 17/068; A61B 17/0682; A61B 17/07292;
(Continued)

(56) References Cited

U.S. PATENT DOCUMENTS 3,054,406 A 9/1962 Usher
3,079,606 A 3/1963 Bobrov et al.
(Continued)

FOREIGN PATENT DOCUMENTS

CA 2282761 A1 9/1998
CA 2 667 434 A1 5/2008
(Continued)

OTHER PUBLICATIONS

Chinese First Office Action corresponding to counterpart Int'l Appln. No. CN 2013107068710 dated Dec. 16, 2016.
(Continued)

*Primary Examiner* — Robert F Long
(74) *Attorney, Agent, or Firm* — Carter, DeLuca & Farrell LLP

(57) ABSTRACT

An anvil assembly includes a circular anvil head that supports a crush ring, an anvil cap that supports an o-ring, and a circular anvil buttress member. The cap connects to the head and is movable relative to the head between approximated and unapproximated positions. The crush ring is spaced from the cap when the cap is in the approximated position and movable into engagement with the cap to move the cap to the unapproximated position. The buttress member includes a body portion and an extension portion. The body portion is supported on the head and the extension portion is secureable between the o-ring and the head when the cap is in the approximated position. The extension portion is releasable from between the o-ring and the head when the cap is disposed in the unapproximated position so that the body portion separates from the head.

17 Claims, 5 Drawing Sheets

Related U.S. Application Data continuation of application No. 14/924,202, filed on Oct. 27, 2015, now Pat. No. 9,895,151, which is a continuation of application No. 13/758,100, filed on Feb. 4, 2013, now Pat. No. 9,192,383.

(51) Int. Cl.
  *A61B 17/068* (2006.01)
  *A61B 17/00* (2006.01)

(52) U.S. Cl.
  CPC ............... *A61B 17/07292* (2013.01); *A61B 2017/00477* (2013.01); *A61B 2017/00862* (2013.01); *Y10T 29/49815* (2015.01)

(58) Field of Classification Search
  CPC .......... A61B 2017/00477; A61B 2017/00862; Y10T 29/49815
  USPC ............... 606/219–221; 227/175.1–182.1
  See application file for complete search history.

(56) References Cited

U.S. PATENT DOCUMENTS

| | | | |
|---|---|---|---|
| 3,124,136 A | 3/1964 | Usher | |
| 3,490,675 A | 1/1970 | Green et al. | |
| 3,499,591 A | 3/1970 | Green | |
| 4,347,847 A | 9/1982 | Usher | |
| 4,354,628 A | 10/1982 | Green | |
| 4,429,695 A | 2/1984 | Green | |
| 4,452,245 A | 6/1984 | Usher | |
| 4,605,730 A | 8/1986 | Shalaby et al. | |
| 4,655,221 A | 4/1987 | Devereux | |
| 4,834,090 A | 5/1989 | Moore | |
| 4,838,884 A | 6/1989 | Dumican et al. | |
| 4,927,640 A | 5/1990 | Dahlinder et al. | |
| 4,930,674 A | 6/1990 | Barak | |
| 5,002,551 A | 3/1991 | Linsky et al. | |
| 5,014,899 A | 5/1991 | Presty et al. | |
| 5,040,715 A | 8/1991 | Green et al. | |
| 5,065,929 A | 11/1991 | Schulze et al. | |
| 5,112,496 A | 5/1992 | Dhawan et al. | |
| 5,205,459 A | 4/1993 | Brinkerhoff et al. | |
| 5,263,629 A | 11/1993 | Trumbull et al. | |
| 5,281,197 A | 1/1994 | Arias et al. | |
| 5,307,976 A | 5/1994 | Olson et al. | |
| 5,312,023 A | 5/1994 | Green et al. | |
| 5,314,471 A | 5/1994 | Brauker et al. | |
| 5,318,221 A | 6/1994 | Green et al. | |
| 5,326,013 A | 7/1994 | Green et al. | |
| 5,332,142 A | 7/1994 | Robinson et al. | |
| 5,344,454 A | 9/1994 | Clarke et al. | |
| 5,392,979 A | 2/1995 | Green et al. | |
| 5,397,324 A | 3/1995 | Carroll et al. | |
| 5,405,072 A | 4/1995 | Zlock et al. | |
| 5,425,745 A | 6/1995 | Green et al. | |
| 5,441,193 A | 8/1995 | Gravener | |
| 5,441,507 A | 8/1995 | Wilk | |
| 5,443,198 A | 8/1995 | Viola et al. | |
| 5,468,253 A | 11/1995 | Bezwada et al. | |
| 5,503,638 A | 4/1996 | Cooper et al. | |
| 5,542,594 A | 8/1996 | McKean et al. | |
| 5,549,628 A | 8/1996 | Cooper et al. | |
| 5,551,622 A * | 9/1996 | Yoon | A61B 17/072 227/176.1 |
| 5,575,803 A | 11/1996 | Cooper et al. | |
| 5,653,756 A | 8/1997 | Clarke et al. | |
| 5,683,809 A | 11/1997 | Freeman et al. | |
| 5,690,675 A | 11/1997 | Sawyer et al. | |
| 5,702,409 A | 12/1997 | Rayburn et al. | |
| 5,752,965 A | 5/1998 | Francis et al. | |
| 5,762,256 A | 6/1998 | Mastri et al. | |
| 5,766,188 A | 6/1998 | Igaki | |
| 5,769,892 A | 6/1998 | Kingwell | |
| 5,782,396 A | 7/1998 | Mastri et al. | |
| 5,799,857 A | 9/1998 | Robertson et al. | |
| 5,810,855 A | 9/1998 | Rayburn et al. | |
| 5,814,057 A | 9/1998 | Oi et al. | |
| 5,833,695 A | 11/1998 | Yoon | |
| 5,843,096 A | 12/1998 | Igaki et al. | |
| 5,871,135 A | 2/1999 | Williamson, IV et al. | |
| 5,895,412 A | 4/1999 | Tucker | |
| 5,895,415 A | 4/1999 | Chow et al. | |
| 5,902,312 A | 5/1999 | Frater et al. | |
| 5,908,427 A | 6/1999 | McKean et al. | |
| 5,915,616 A | 6/1999 | Viola et al. | |
| 5,931,847 A | 8/1999 | Billner et al. | |
| 5,957,363 A | 9/1999 | Heck | |
| 5,964,731 A * | 10/1999 | Kovelman | A61M 5/3271 604/110 |
| 5,964,774 A | 10/1999 | McKean et al. | |
| 5,997,895 A | 12/1999 | Narotam et al. | |
| 6,017,356 A * | 1/2000 | Frederick | A61B 17/3417 606/167 |
| 6,019,791 A | 2/2000 | Wood | |
| 6,030,392 A | 2/2000 | Dakov | |
| 6,032,849 A | 3/2000 | Mastri et al. | |
| 6,045,560 A | 4/2000 | McKean et al. | |
| 6,063,097 A | 5/2000 | Oi et al. | |
| 6,080,169 A | 6/2000 | Turtel | |
| 6,099,551 A | 8/2000 | Gabbay | |
| 6,149,667 A | 11/2000 | Hovland et al. | |
| 6,155,265 A | 12/2000 | Hammerslag | |
| 6,210,439 B1 | 4/2001 | Firmin et al. | |
| 6,214,020 B1 | 4/2001 | Mulhauser et al. | |
| 6,241,139 B1 | 6/2001 | Milliman et al. | |
| 6,258,107 B1 | 7/2001 | Balazs et al. | |
| 6,267,772 B1 | 7/2001 | Mulhauser et al. | |
| 6,270,484 B1 * | 8/2001 | Yoon | A61B 17/3494 604/264 |
| 6,273,897 B1 | 8/2001 | Dalessandro et al. | |
| 6,280,453 B1 | 8/2001 | Kugel et al. | |
| 6,299,631 B1 | 10/2001 | Shalaby | |
| 6,312,457 B1 | 11/2001 | DiMatteo et al. | |
| 6,312,474 B1 | 11/2001 | Francis et al. | |
| 6,325,810 B1 | 12/2001 | Hamilton et al. | |
| 6,436,030 B2 | 8/2002 | Rehil | |
| 6,454,780 B1 | 9/2002 | Wallace | |
| 6,461,368 B2 | 10/2002 | Fogarty et al. | |
| 6,503,257 B2 | 1/2003 | Grant et al. | |
| 6,514,283 B2 | 2/2003 | DiMatteo et al. | |
| 6,517,566 B1 | 2/2003 | Hovland et al. | |
| 6,551,356 B2 | 4/2003 | Rousseau | |
| 6,568,398 B2 | 5/2003 | Cohen | |
| 6,592,597 B2 | 7/2003 | Grant et al. | |
| 6,610,006 B1 | 8/2003 | Amid et al. | |
| 6,638,285 B2 | 10/2003 | Gabbay | |
| 6,652,594 B2 | 11/2003 | Francis et al. | |
| 6,656,193 B2 | 12/2003 | Grant et al. | |
| 6,669,735 B1 | 12/2003 | Pelissier | |
| 6,677,258 B2 | 1/2004 | Carroll et al. | |
| 6,685,714 B2 | 2/2004 | Rousseau | |
| 6,702,828 B2 | 3/2004 | Whayne | |
| 6,704,210 B1 | 3/2004 | Myers | |
| 6,723,114 B2 | 4/2004 | Shalaby | |
| 6,726,706 B2 | 4/2004 | Dominguez | |
| 6,736,823 B2 | 5/2004 | Darois et al. | |
| 6,736,854 B2 | 5/2004 | Vadurro et al. | |
| 6,746,458 B1 | 6/2004 | Cloud | |
| 6,773,458 B1 | 8/2004 | Brauker et al. | |
| 6,896,684 B2 | 5/2005 | Monassevitch et al. | |
| 6,927,315 B1 | 8/2005 | Heinecke et al. | |
| 6,939,358 B2 | 9/2005 | Palacios et al. | |
| 6,946,196 B2 | 9/2005 | Foss | |
| 6,959,851 B2 | 11/2005 | Heinrich | |
| 7,025,772 B2 | 4/2006 | Gellman et al. | |
| 7,060,087 B2 | 6/2006 | DiMatteo et al. | |
| 7,087,065 B2 | 8/2006 | Ulmsten et al. | |
| 7,108,701 B2 | 9/2006 | Evens et al. | |
| 7,128,748 B2 | 10/2006 | Mooradian et al. | |
| 7,141,055 B2 | 11/2006 | Abrams et al. | |
| 7,147,138 B2 | 12/2006 | Shelton, IV | |
| 7,160,299 B2 | 1/2007 | Baily | |
| 7,179,268 B2 | 2/2007 | Roy et al. | |

(56) References Cited

U.S. PATENT DOCUMENTS

| | | | |
|---|---|---|---|
| 7,210,810 B1 | 5/2007 | Iversen et al. |
| 7,232,449 B2 | 6/2007 | Sharkawy et al. |
| 7,241,300 B2 | 7/2007 | Sharkawy et al. |
| 7,307,031 B2 | 12/2007 | Carroll et al. |
| 7,311,720 B2 | 12/2007 | Mueller et al. |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,594,921 B2 | 9/2009 | Browning |
| 7,604,151 B2 | 10/2009 | Hess et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,837,080 B2 * | 11/2010 | Schwemberger .. A61B 17/1155 227/176.1 |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,966,799 B2 | 6/2011 | Morgan |
| 7,967,179 B2 | 6/2011 | Olson et al. |
| 7,988,027 B2 | 8/2011 | Olson et al. |
| 8,011,550 B2 | 9/2011 | Aranyi et al. |
| 8,016,177 B2 | 9/2011 | Bettuchi et al. |
| 8,016,178 B2 | 9/2011 | Olson et al. |
| 8,028,883 B2 | 10/2011 | Stopek |
| 8,033,983 B2 | 10/2011 | Chu et al. |
| 8,062,330 B2 | 11/2011 | Prommersberger et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,127,975 B2 | 3/2012 | Olson et al. |
| 8,146,791 B2 | 4/2012 | Bettuchi et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,192,460 B2 | 6/2012 | Orban, III et al. |
| 8,210,414 B2 | 7/2012 | Bettuchi et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,348,126 B2 | 1/2013 | Olson et al. |
| 8,348,130 B2 | 1/2013 | Shah et al. |
| 8,353,438 B2 * | 1/2013 | Baxter, III ......... A61B 1/00087 606/1 |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,388,633 B2 | 3/2013 | Rousseau et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,413,871 B2 | 4/2013 | Racenet et al. |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,584,920 B2 | 11/2013 | Hodgkinson |
| 8,590,762 B2 | 11/2013 | Hess et al. |
| 8,616,430 B2 | 12/2013 | (Prommersberger) Stopek |
| 8,631,989 B2 | 1/2014 | Aranyi et al. |
| 8,668,129 B2 | 3/2014 | Olson |
| 8,684,250 B2 | 4/2014 | Bettuchi et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek |
| 9,016,544 B2 | 4/2015 | Hodgkinson et al. |
| 9,027,817 B2 | 5/2015 | Milliman et al. |
| 9,113,885 B2 * | 8/2015 | Hodgkinson ......... A61B 17/32 |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek |
| 9,402,627 B2 | 8/2016 | Stevenson et al. |
| 9,414,839 B2 | 8/2016 | Penna |
| 9,433,412 B2 | 9/2016 | Bettuchi et al. |

(56) References Cited

U.S. PATENT DOCUMENTS

| | | |
|---|---|---|
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,486,215 B2 | 11/2016 | Olson et al. |
| 9,504,470 B2 | 11/2016 | Milliman |
| 9,572,576 B2 | 2/2017 | Hodgkinson et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,895,151 B2 | 2/2018 | Milliman |
| 9,931,116 B2 | 4/2018 | Racenet et al. |
| 10,022,125 B2 | 7/2018 | (Prommersberger) Stopek |
| 10,098,639 B2 | 10/2018 | Hodgkinson |
| 10,111,659 B2 | 10/2018 | Racenet et al. |
| 10,154,840 B2 | 12/2018 | Viola et al. |
| 10,595,872 B2 | 3/2020 | Milliman |
| 11,284,896 B2 * | 3/2022 | Williams ......... A61B 17/07292 |
| 2002/0028243 A1 | 3/2002 | Masters |
| 2002/0091397 A1 | 7/2002 | Chen |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2003/0065345 A1 | 4/2003 | Weadock |
| 2003/0083676 A1 | 5/2003 | Wallace |
| 2003/0120284 A1 | 6/2003 | Palacios et al. |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0196668 A1 | 10/2003 | Harrison et al. |
| 2003/0208231 A1 | 11/2003 | Williamson et al. |
| 2004/0107006 A1 | 6/2004 | Francis et al. |
| 2004/0116945 A1 | 6/2004 | Sharkawy et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0187576 A1 | 8/2005 | Whitman et al. |
| 2005/0228446 A1 | 10/2005 | Mooradian et al. |
| 2005/0251164 A1 | 11/2005 | Gifford et al. |
| 2006/0004407 A1 | 1/2006 | Hiles et al. |
| 2006/0025816 A1 * | 2/2006 | Shelton ............ A61B 17/07207 606/215 |
| 2006/0085030 A1 | 4/2006 | Bettuchi et al. |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0219752 A1 | 10/2006 | Arad et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles et al. |
| 2008/0216855 A1 | 9/2008 | Nasca |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0005809 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 * | 8/2009 | Huitema ......... A61B 17/07292 227/176.1 |
| 2009/0218384 A1 | 9/2009 | Aranyi |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0089220 A1 | 4/2011 | Ingmanson et al. |
| 2011/0114700 A1 | 5/2011 | Baxter, III et al. |
| 2011/0125091 A1 * | 5/2011 | Abbate ............... A61K 9/0043 606/199 |
| 2011/0174099 A1 | 7/2011 | Ross et al. |
| 2011/0215132 A1 | 9/2011 | Aranyi et al. |
| 2011/0278346 A1 | 11/2011 | Hull et al. |
| 2011/0278347 A1 | 11/2011 | Olson et al. |
| 2011/0282446 A1 * | 11/2011 | Schulte ............... A61B 17/115 623/11.11 |
| 2012/0012638 A1 | 1/2012 | Huang |
| 2012/0074199 A1 | 3/2012 | Olson et al. |
| 2012/0080336 A1 | 4/2012 | Shelton, IV et al. |
| 2012/0145767 A1 | 6/2012 | Shah et al. |

(56) References Cited

U.S. PATENT DOCUMENTS

| | | |
|---|---|---|
| 2012/0187179 A1 | 7/2012 | Gleiman |
| 2012/0241499 A1 | 9/2012 | Baxter, III et al. |
| 2012/0241505 A1* | 9/2012 | Alexander, III ... A61B 17/0643 |
| | | 227/179.1 |
| 2012/0273547 A1 | 11/2012 | Hodgkinson et al. |
| 2013/0037596 A1 | 2/2013 | Bear et al. |
| 2013/0105548 A1 | 5/2013 | Hodgkinson et al. |
| 2013/0105553 A1 | 5/2013 | (Tarinelli) Racenet et al. |
| 2013/0112732 A1 | 5/2013 | Aranyi et al. |
| 2013/0112733 A1 | 5/2013 | Aranyi et al. |
| 2013/0146641 A1 | 6/2013 | Shelton, IV et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze et al. |
| 2013/0181031 A1 | 7/2013 | Olson et al. |
| 2013/0193186 A1 | 8/2013 | (Tarinelli) Racenet et al. |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0209659 A1 | 8/2013 | Racenet et al. |
| 2013/0221062 A1 | 8/2013 | Hodgkinson |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0277411 A1 | 10/2013 | Hodgkinson et al. |
| 2013/0306707 A1 | 11/2013 | Viola et al. |
| 2013/0310873 A1 | 11/2013 | Stopek (nee Prommersberger) et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0061281 A1 | 3/2014 | Hodgkinson |
| 2014/0084042 A1 | 3/2014 | (Prommersberger) Stopek |
| 2014/0097224 A1 | 4/2014 | Prior |
| 2014/0117066 A1 | 5/2014 | Aranyi et al. |
| 2014/0130330 A1 | 5/2014 | Olson et al. |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |
| 2014/0158742 A1 | 6/2014 | Stopek (nee Prommersberger) et al. |
| 2014/0166721 A1 | 6/2014 | Stevenson et al. |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0224686 A1 | 8/2014 | Aronhalt et al. |
| 2014/0239046 A1 | 8/2014 | Milliman |
| 2014/0239047 A1 | 8/2014 | Hodgkinson et al. |
| 2014/0252062 A1* | 9/2014 | Mozdzierz ......... A61B 17/1155 |
| | | 227/175.1 |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0231409 A1 | 8/2015 | Racenet et al. |
| 2015/0305743 A1 | 10/2015 | Casasanta et al. |
| 2015/0327864 A1 | 11/2015 | Hodgkinson et al. |
| 2015/0351758 A1 | 12/2015 | Shelton, IV et al. |
| 2015/0351760 A1 | 12/2015 | Vendely |
| 2015/0351762 A1 | 12/2015 | Vendely |
| 2016/0022268 A1 | 1/2016 | Prior |
| 2016/0045200 A1 | 2/2016 | Milliman |
| 2016/0058451 A1 | 3/2016 | (Tarinelli) Racenet et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0256166 A1 | 9/2016 | (Prommersberger) Stopek |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0151030 A1* | 6/2017 | Penna ..................... A61B 50/30 |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | (Prommersberger) Stopek |
| 2019/0021734 A1 | 1/2019 | Hodgkinson |
| 2019/0059878 A1 | 2/2019 | (Tarinelli) Racenet et al. |
| 2019/0083087 A1 | 3/2019 | Viola et al. |
| 2020/0000475 A1* | 1/2020 | Williams ............ A61B 17/1155 |

FOREIGN PATENT DOCUMENTS

| | | |
|---|---|---|
| DE | 1602563 U | 3/1950 |
| DE | 19924311 A1 | 11/2000 |
| EP | 0327022 A2 | 8/1989 |
| EP | 0594148 A1 | 4/1994 |
| EP | 0667119 A1 | 8/1995 |
| EP | 1064883 A1 | 1/2001 |
| EP | 1256317 A2 | 11/2002 |
| EP | 1256318 A1 | 11/2002 |
| EP | 1520525 A1 | 4/2005 |
| EP | 1621141 A2 | 2/2006 |
| EP | 1702570 A1 | 9/2006 |
| EP | 1759640 A2 | 3/2007 |
| EP | 1815804 A2 | 8/2007 |
| EP | 1825820 A1 | 8/2007 |
| EP | 1929958 A2 | 6/2008 |
| EP | 1994890 A1 | 11/2008 |
| EP | 2005894 A2 | 12/2008 |
| EP | 2005895 A2 | 12/2008 |
| EP | 2090231 A1 | 8/2009 |
| EP | 2090244 A2 | 8/2009 |
| EP | 2090252 A2 | 8/2009 |
| EP | 2236098 A2 | 10/2010 |
| EP | 2236099 A1 | 10/2010 |
| EP | 2292276 A2 | 3/2011 |
| EP | 2311386 A2 | 4/2011 |
| EP | 2436348 A1 | 4/2012 |
| EP | 2462880 B1 | 6/2012 |
| EP | 2517637 A1 | 10/2012 |
| EP | 2586380 A1 | 5/2013 |
| EP | 2604195 A1 | 6/2013 |
| EP | 2604197 A2 | 6/2013 |
| EP | 2620105 A1 | 7/2013 |
| EP | 2620106 A2 | 7/2013 |
| EP | 2630922 A1 | 8/2013 |
| EP | 2644125 A2 | 10/2013 |
| EP | 2762091 A2 | 8/2014 |
| EP | 2769687 A1 | 8/2014 |
| EP | 2008595 B1 | 4/2016 |
| EP | 2198787 B1 | 3/2017 |
| JP | 2000166933 A | 6/2000 |
| JP | 2002202213 A | 7/2002 |

(56) References Cited

FOREIGN PATENT DOCUMENTS

| JP | 2007124166 A | 5/2007 |
|---|---|---|
| WO | 9005489 A1 | 5/1990 |
| WO | 95/16221 A1 | 6/1995 |
| WO | 9622055 A1 | 7/1996 |
| WO | 9701989 A1 | 1/1997 |
| WO | 9713463 A1 | 4/1997 |
| WO | 9817180 A1 | 4/1998 |
| WO | 98/38923 A1 | 9/1998 |
| WO | 9945849 A1 | 9/1999 |
| WO | 03082126 A1 | 10/2003 |
| WO | 03088845 A2 | 10/2003 |
| WO | 03094743 A1 | 11/2003 |
| WO | 03105698 A2 | 12/2003 |
| WO | 2005079675 A2 | 9/2005 |
| WO | 2006023578 A2 | 3/2006 |
| WO | 2006044490 A2 | 4/2006 |
| WO | 2006083748 A1 | 8/2006 |
| WO | 2007121579 A1 | 11/2007 |
| WO | 2008057281 A2 | 5/2008 |
| WO | 2008109125 A1 | 9/2008 |
| WO | 2010075298 A2 | 7/2010 |
| WO | 2011143183 A2 | 11/2011 |
| WO | 2012044848 A1 | 4/2012 |

OTHER PUBLICATIONS

Chinese First Office Action corresponding to counterpart Int'l Appln. No. CN 201310646606.8 dated Dec. 23, 2016.
Japanese Office Action corresponding to counterpart Int'l Appln. No. JP 2013-000321 dated Jan. 4, 2017.
Extended European Search Report corresponding to counterpart Int'l Appln. No. EP 16 16 6367.9 dated Jan. 16, 2017.
Australian Examination Report No. 1 corresponding to counterpart Int'l Appln. No. AU 2013206777 dated Feb. 1, 2017.
Chinese Second Office Action corresponding to counterpart Int'l Appln. No. CN 2013103036903 dated Feb. 23, 2017.
Japanese Office Action corresponding to counterpart Int'l Appln. No. JP 2013-175379 dated Mar. 1, 2017.
Chinese First Office Action corresponding to counterpart Int'l Appln. No. CN 201410028462.4 dated Mar. 2, 2017.
Chinese First Office Action corresponding to counterpart Int'l Appln. No. CN 201410084070 dated Mar. 13, 2017.
Extended European Search Report corresponding to counterpart Int'l Appln. No. EP 16 19 6549.6 dated Mar. 17, 2017.
Japanese Office Action corresponding to counterpart Int'l Appln. No. JP 2013-147701 dated Mar. 21, 2017.
Australian Examination Report No. 1 corresponding to counterpart Int'l Appln. No. AU 2013206804 dated Mar. 21, 2017.
Australian Examination Report No. 1 corresponding to counterpart Int'l Appln. No. AU 2013211499 dated May 4, 2017.
Australian Examination Report No. 1 corresponding to counterpart Int'l Appln. No. AU 2014201008 dated May 23, 2017.
European Office Action corresponding to counterpart Int'l Appln. No. EP 14 17 2681.0 dated May 13, 2016.
Chinese Office Action corresponding to counterpart Int'l Appln. No. CN 201210545228 dated Jun. 29, 2016.
Japanese Office Action corresponding to counterpart Int'l Appln. No. JP 2012-250058 dated Jun. 29, 2016.
Office Action corresponding to counterpart Int'l Appln. No. EP 14 15 7997.9 dated Jun. 29, 2016.
Office Action corresponding to counterpart Int'l Appln. No. CA 2,712,617 dated Jun. 30, 2016.
Chinese First Office Action corresponding to counterpart Int'l Appln. No. CN 2013103036903 dated Jun. 30, 2016.
Australian Patent Examination Report No. 1 corresponding to counterpart Int'l Appln. No. AU 2012250278 dated Jul. 10, 2016.
Australian Patent Examination Report No. 1 corresponding to counterpart Int'l Appln. No. AU 2012244382 dated Jul. 10, 2016.
Japanese Office Action corresponding to counterpart Int'l Appln. No. JP 2012-255242 dated Jul. 26, 2016.
Japanese Office Action corresponding to counterpart Int'l Appln. No. JP 2012-268668 dated Jul. 27, 2016.
European Office Action corresponding to counterpart Int'l Appln. No. EP 14 15 2060.1 dated Aug. 4, 2016.
European Office Action corresponding to counterpart Int'l Appln. No. EP 12 16 5609.4 dated Aug. 5, 2016.
European Office Action corresponding to counterpart Int'l Appln. No. EP 15 15 2392.5 dated Aug. 8, 2016.
Japanese Office Action corresponding to counterpart Int'l Appln. No. JP 2013-003624 dated Aug. 25, 2016.
Australian Patent Examination Report No. 1 corresponding to counterpart Int'l Appln. No. AU 2012261752 dated Sep. 3, 2016.
Japanese Office Action corresponding to counterpart Int'l Appln. No. JP 2014-252703 dated Sep. 26, 2016.
European Office Action corresponding to counterpart Int'l Appln. No. EP 12 19 8776.2 dated Sep. 12, 2016.
Japanese Office Action corresponding to counterpart Int'l Appln. No. JP 2013-000321 dated Sep. 13, 2016.
Chinese Second Office Action corresponding to counterpart Int'l Appln. No. CN 201310353628.5 dated Sep. 26, 2016.
European Office Action corresponding to counterpart Int'l Appln. No. EP 12 15 2541.4 dated Sep. 27, 2016.
Australian Patent Examination Report No. 1 corresponding to counterpart Int'l Appln. No. AU 2012268923 dated Sep. 28, 2016.
Australian Examination Report issued in Australian Appln. No. 2014200109 dated Jul. 20, 2017.
Chinese Notification of Reexamination corresponding to counterpart Int'l Appln. No. CN 201010517292.8 dated Jun. 2, 2015.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to EP 12 19 1035.0, completed Jan. 11, 2013 and dated Jan. 18, 2013; 7 pages.
Extended European Search Report corresponding to EP 12 18 6175.1, completed Jan. 15, 2013 and dated Jan. 23, 2013; 7 pages.
Extended European Search Report corresponding to EP 12 19 1114.3, completed Jan. 23, 2013 and dated Jan. 31, 2013; Wpages.
Extended European Search Report corresponding to EP 12 19 2224.9, completed Mar. 14, 2013 and dated Mar. 26, 2013; 8 pages.
Extended European Search Report corresponding to EP 12 19 6911.7, completed Apr. 18, 2013 and dated Apr. 24, 2013; 8 pages.
Extended European Search Report corresponding to EP 12 19 6904.2, completed Mar. 28, 2013 and dated Jul. 26, 2013; 8 pages.
Extended European Search Report corresponding to EP 12 19 8749.9, completed May 21, 2013 and dated May 31, 2013; 8 pages.
Extended European Search Report corresponding to EP 07 00 5842.5, completed May 13, 2013 and dated May 29, 2013; 7 pages.

(56) References Cited

OTHER PUBLICATIONS

Extended European Search Report corresponding to EP 12 19 8776.2, completed May 16, 2013, and dated May 27, 2013; 8 pages.
Extended European Search Report corresponding to EP 13 15 6297.7, completed Jun. 4, 2013 and dated Jun. 13, 2013; 7 pages.
Extended European Search Report corresponding to EP 13 17 3985.6, completed Aug. 19, 2013 and dated Aug. 28, 2013; 6 pages.
Extended European Search Report corresponding to EP 13 17 3986.4, completed Aug. 20, 2013 and dated Aug. 29, 2013; 7 pages.
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
Extended European Search Report corresponding to EP 13 17 7437.4, completed Sep. 11, 2013 and dated Sep. 19, 2013; (6 pp).
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to counterpart Int'l Appln No. EP 14 15 2060.1 dated Aug. 14, 2015.
Japanese Office Action corresponding to counterpart Int'l Appln. No. JP 2014-216989 dated Sep. 11, 2015.
Canadian First Office Action corresponding to counterpart Int'l Appln. No. CA 2,686,105 dated Sep. 17, 2015.
Office Action corresponding to counterpart Int'l Appln. No. JP 2012-040188 dated Oct. 21, 2015.
Communication corresponding to counterpart Int'l Appln. No. EP 13 17 6895.4 dated Nov. 5, 2015.
Chinese First Office Action corresponding to counterpart Int'l Appln. No. CN 201210544552 dated Nov. 23, 2015.
Chinese First Office Action corresponding to counterpart Int'l Appln. No. CN 201210545228 dated Nov. 30, 2015.
Extended European Search Report corresponding to counterpart Int'l Appln. No. EP 15 18 0491.1 dated Dec. 9, 2015.
Extended European Search Report corresponding to counterpart Int'l Appln. No. EP 15 18 3819.0 dated Dec. 11, 2015.
Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Int'l Appln. No. EP 12 19 8776.2 dated Jan. 19, 2016.
Extended European Search Report corresponding to counterpart Int'l Appln. No. EP 15 17 4146.9 dated Jan. 20, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 dated Feb. 22, 2016.
Extended European Search Report corresponding to counterpart Int'l Appln. No. EP 12 19 8753.1 dated Feb. 24, 2016.
Chinese First Office Action corresponding to counterpart Int'l Appln. No. CN 201410449019.4 dated Mar. 30, 2016.
Extended European Search Report corresponding to counterpart Int'l Appln. No. EP 16150232.3, dated Apr. 12, 2016.
European Office Action corresponding to counterpart Int'l Appln. No. EP 11 18 3256.4 dated Apr. 20, 2016.
Australian Examination Report No. 1 corresponding to counterpart Int'l Appln. No. AU 2012244169 dated May 10, 2016.
European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 201.
Japanese Office Action corresponding to counterpart Int'l Appln. No. JP 2012-040188 dated May 17, 2016.
Australian Examination Report No. 1 corresponding to counterpart Int'l Appln. No. AU 2012244380 dated May 20, 2016.
Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
Extended European Search Report corresponding to counterpart Int'l Appln. No. EP 16 15 3647.9 dated Jun. 3, 2016.
European Search Report corresponding to EP 05 02 2585.3, completed Jan. 25, 2006 and dated Feb. 3, 2006; 4 pages.
European Search Report corresponding to EP 06 00 4598, completed Jun. 22, 2006; 2 pages.
European Search Report corresponding to EP 06 01 6962.0, completed Jan. 3, 2007 and dated Jan. 11, 2007; 10 pages.
International Search Report corresponding to International Application No. PCT/US2005/ 36740, completed Feb. 20, 2007 and dated Mar. 23, 2007; 8 pages.
International Search Report corresponding to International Application No. PCT/US2007/022713, completed Apr. 21, 2008 and dated May 15, 2008; 1 page.
International Search Report corresponding to International Application No. PCT/US2008/002981, completed Jun. 9, 2008 and dated Jun. 26, 2008; 2 pages.
Search Report corresponding to EP 08 25 1779, completed Jul. 14, 2008 and dated Jul. 23, 2008; 5 pages.
European Search Report corresponding to EP 08 25 1989.3, completed Mar. 11, 2010 and dated Mar. 24, 2010; 6 pages.
European Search Report corresponding to EP 10 25 0639.1, completed Jun. 17, 2010 and dated Jun. 28, 2010; 7 pages.
European Search Report corresponding to EP 10 25 0715.9, completed Jun. 30, 2010 and dated Jul. 20, 2010; 3 pages.
European Search Report corresponding to EP 05 80 4382.9, completed Oct. 5, 2010 and dated Oct. 12, 2010; 3 pages.
European Search Report corresponding to EP 10 25 1437.9, completed Nov. 22, 2010 and dated Dec. 16, 2010; 3 pages.
European Search Report corresponding to EP 09 25 2897.5, completed Feb. 7, 2011 and dated Feb. 15, 2011; 3 pages.
European Search Report corresponding to EP 10 25 0642.5, completed Mar. 25, 2011 and dated Apr. 4, 2011; 4 pages.
European Search Report corresponding to EP 11 18 8309.6, completed Dec. 15, 2011 and dated Jan. 12, 2012; 3 pages.
European Search Report corresponding to EP 12 15 2229.6, completed Feb. 23, 2012 and dated Mar. 1, 2012; 4 pages.
European Search Report corresponding to EP 12 15 0511.9, completed Apr. 16, 2012 and dated Apr. 24, 2012; 7 pages.
European Search Report corresponding to EP 12 15 2541 4, completed Apr. 23, 2012 and dated May 3, 2012; 10 pages.
European Search Report corresponding to EP 12 16 5609.4, completed Jul. 5, 2012 and dated Jul. 13, 2012; 8 pages.
European Search Report corresponding to EP 12 15 8861.0, completed Jul. 17, 2012 and dated Jul. 24, 2012; 9 pages.
European Search Report corresponding to EP 12 16 5878.5, completed Jul. 24, 2012 and dated Aug. 6, 2012; 8 pages.
Extended European Search Report issued in corresponding European Appln. No. 14153609.4 dated Jul. 14, 2017.

(56) References Cited

OTHER PUBLICATIONS

Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 08 72 6500.5, completed Feb. 20, 2014 and dated Mar. 3, 2014; (7 pp).
Extended European Search Report corresponding to EP 13 19 5919.9, completed Feb. 10, 2014 and dated Mar. 3, 2014; (7 pp).
Extended European Search Report corresponding to EP 13 19 2123.1, completed Jan. 30, 2014 and dated Feb. 10, 2014; (8 pp).
Extended European Search Report corresponding to EP 13 19 6816.6, completed Mar. 28, 2014 and dated Apr. 9, 2014; (9 pp).
Extended European Search Report corresponding to EP 13 19 4995.0, completed Jun. 5, 2014 and dated Jun. 16, 2014; (5 pp).
Extended European Search Report corresponding to EP 13 19 5019.8, completed Mar. 14, 2014 and dated Mar. 24, 2014; (7 pp).
Extended European Search Report corresponding to EP 13 19 2111.6, completed Feb. 13, 2014 and dated Feb. 27, 2014; (10 pp).
Extended European Search Report corresponding to EP 13 19 7958.5, completed Apr. 4, 2014 and dated Apr. 15, 2014; (8 pp).
Extended European Search Report corresponding to EP 14 15 6342.9, completed Jul. 22, 2014 and dated Jul. 29, 2014; (8 pp).
Extended European Search Report corresponding to EP 14 15 7195.0, completed Jun. 5, 2014 and dated Jun. 18, 2014; (9 pp).

\* cited by examiner

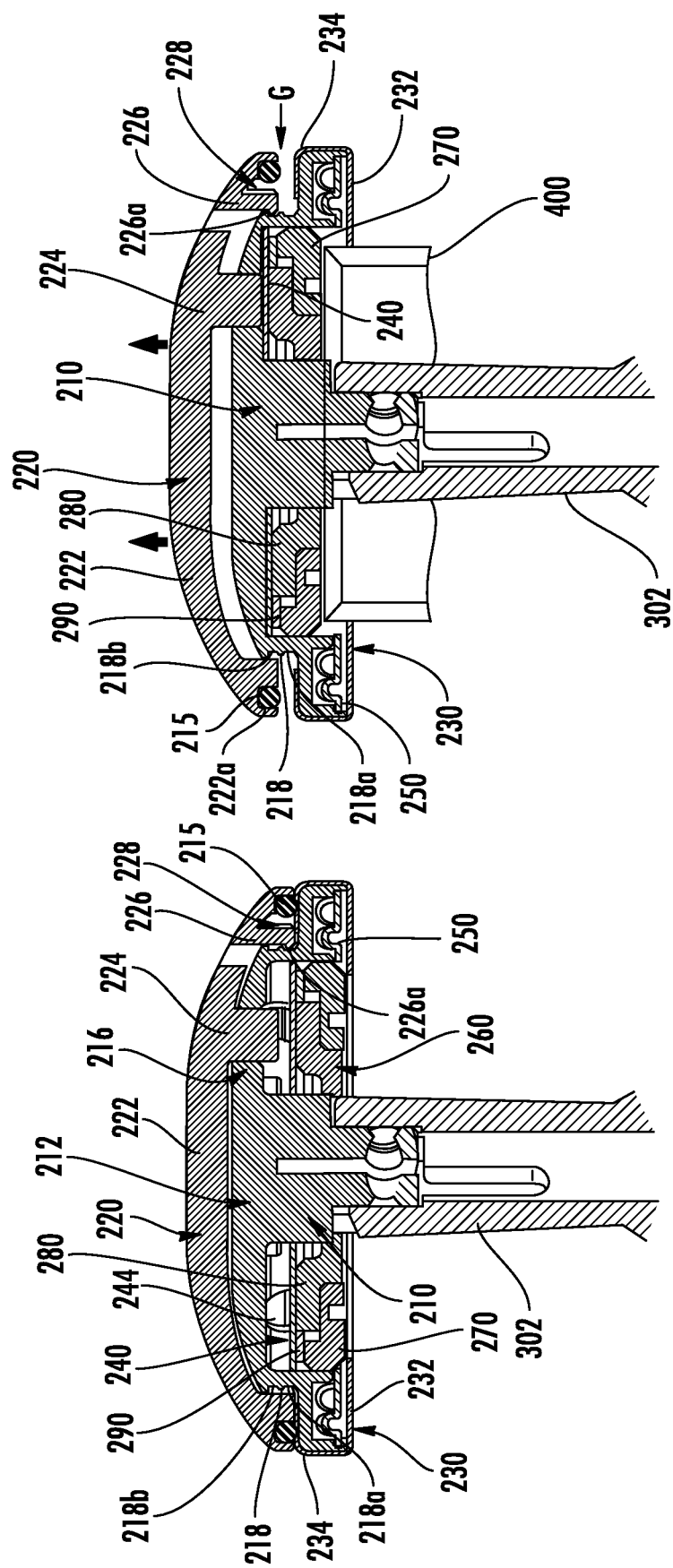

CIRCULAR STAPLING DEVICE INCLUDING BUTTRESS MATERIAL

CROSS-REFERENCE TO RELATED APPLICATIONS

This application is a continuation of U.S. patent application Ser. No. 15/875,419, filed Jan. 19, 2018, which is a continuation of U.S. patent application Ser. No. 14/924,202, filed Oct. 27, 2015, now U.S. Pat. No. 9,895,151, which is a continuation of U.S. patent application Ser. No. 13/758,100, filed Feb. 4, 2013, now U.S. Pat. No. 9,192,383, the entire disclosure of each of which is hereby incorporated by reference herein.

TECHNICAL FIELD

The present disclosure relates to surgical stapling devices and, more particularly, to structures and methods for removably attaching buttress material to circular surgical stapling devices for use in anastomosis procedures.

BACKGROUND

Fasteners have been used to replace suturing when joining various body structures such as, for example, the bowel or bronchus. Surgical stapling devices employed to apply these fasteners are generally designed to simultaneously cut and seal tissue to reduce the time and risks involved with anastomosis procedures.

Circular surgical stapling devices are employed by surgeons to sequentially or simultaneously apply one or more surgical fasteners, e.g., staples or two-part fasteners, to body tissue for the purpose of joining segments of body tissue together and/or for the creation of anastomoses. Circular surgical stapling devices generally include an annular fastener cartridge assembly that supports a plurality of annular rows of fasteners, an annular anvil assembly operatively associated with the fastener cartridge assembly which provides a surface against which the fasteners are formed upon a firing of the circular stapling device, and an annular blade for cutting tissue.

For most procedures, the use of bare fasteners, with the fasteners in direct contact with the patient's tissue, is generally acceptable. The integrity of the tissue will normally serve to prevent the fasteners from tearing out of the tissue and compromising the sealing before healing has occurred. However, in some surgical operations buttress materials are employed by surgeons in combination with circular stapling devices to bridge, repair and/or reinforce tissue defects within a patient. In particular, buttress materials reduce the trauma suffered by the patient, reduce the instances of leakage, reduce the instances of bleeding, and create a relatively strong bond between adjacent body tissues.

Accordingly, there is a need for reliably and removably attaching buttress material onto a circular stapling device so that the buttress material does not interfere with the operation of the device, remains on the device until after the fasteners are fired, and is convenient and easy to install and use.

SUMMARY

According to one aspect, a circular stapling device includes a handle assembly, an elongate body that extends from the handle assembly, and an end effector mounted on a distal end of the elongate body and including a cartridge assembly and an anvil assembly.

The anvil assembly includes a circular anvil head that supports a crush ring, an anvil cap that supports an o-ring, and a circular anvil buttress member. In embodiments, the o-ring is formed of an elastomeric material including nitrile.

The anvil cap connects to the anvil head and is movable relative to the anvil head between an approximated position and an unapproximated position. The crush ring is spaced from the anvil cap when the anvil cap is disposed in the approximated position and movable into engagement with the anvil cap to move the anvil cap to the unapproximated position. The anvil cap defines a groove in a bottom surface of the anvil cap and the o-ring is secured within the groove. The o-ring is disposed in a compressed condition when the anvil cap is disposed in the approximated position and an uncompressed condition when the anvil cap is disposed in the unapproximated position.

The anvil cap includes a snap feature and the anvil head defines a first recess and a second recess. The snap feature is selectively positionable within one of the first recess and the second recess. The snap feature is positionable within the first recess when the anvil cap is disposed in the approximated position and is positionable within the second recess when the anvil cap is disposed in the unapproximated position. The first recess and the second recess are separated by a ramped partition. The snap feature cams over the ramped feature as the anvil cap moves from the approximated position to the unapproximated position. The snap feature flexes outwardly from the first recess as the snap feature cams over the ramped partition and flexes inwardly into the second recess after camming over the ramped partition. The snap feature maintains the anvil cap secured to the anvil head when the snap feature is disposed in the second recess.

The circular anvil buttress member includes a body portion and an extension portion that extends from the body portion. The body portion is supported on a tissue engaging surface of the anvil head. The extension portion is secureable between the o-ring and the anvil head when the anvil cap is disposed in the approximated position. The extension portion is releasable from between the o-ring and the anvil head when the anvil cap is disposed in the unapproximated position so that the body portion separates from the tissue engaging surface of the anvil head. The extension portion includes one or more tabs. The o-ring is compressed against the one or more tabs when the anvil cap is disposed in the approximated position to maintain the body portion supported on the tissue engaging surface of the anvil head.

In another aspect, then anvil assembly includes a circular anvil head that supports a crush ring, and anvil cap that connects to the anvil head and supports an o-ring, and a circular anvil buttress member.

The anvil cap is movable relative to the anvil head between an approximated position and an unapproximated position. The crush ring is spaced from the anvil cap when the anvil cap is disposed in the approximated position and movable into engagement with the anvil cap to move the anvil cap to the unapproximated position. The anvil cap defines a groove in a bottom surface of the anvil cap. The o-ring is secured within the groove. The o-ring is disposed in a compressed condition when the anvil cap is disposed in the approximated position and in an uncompressed condition when the anvil cap is disposed in the unapproximated position. In embodiments, the o-ring is formed of an elastomeric material including nitrile.

The anvil cap includes a snap feature and the anvil head defines a first recess and a second recess. The snap feature is selectively positionable within one of the first recess and the second recess. The snap feature is positionable within the first recess when the anvil cap is disposed in the approximated position and is positionable within the second recess when the anvil cap is disposed in the unapproximated position. The first recess and the second recess are separated by a ramped partition. The snap feature cams over the ramped feature as the anvil cap moves from the approximated position to the unapproximated position. The snap feature flexes outwardly from the first recess as the snap feature cams over the ramped partition and flexes inwardly into the second recess after camming over the ramped partition. The snap feature maintains the anvil cap secured to the anvil head when the snap feature is disposed in the second recess.

The circular anvil buttress member includes a body portion and an extension portion that extends from the body portion. The body portion is supported on a tissue engaging surface of the anvil head. The extension portion is secureable between the o-ring and the anvil head when the anvil cap is disposed in the approximated position. The extension portion is releasable from between the o-ring and the anvil head when the anvil cap is disposed in the unapproximated position so that the body portion separates from the tissue engaging surface of the anvil head. The extension portion includes one or more tabs. The o-ring is compressed against the one or more tabs when the anvil cap is disposed in the approximated position to maintain the body portion supported on the tissue engaging surface of the anvil head.

According to yet another aspect, the present disclosure is directed to a method for releasing an anvil buttress member from an anvil assembly of a circular stapling device. The method includes the step of providing a circular stapling device including an elongate member having an end effector mounted on a distal end of the elongate body. The end effector includes an anvil assembly that includes an anvil head and an anvil cap that supports an o-ring. The anvil assembly includes an extension portion of an anvil buttress member secured between the o-ring and the anvil head so that a body portion of the anvil buttress member is supported on a tissue engaging surface of the anvil head. The method involves moving the o-ring relative to anvil head to release the anvil buttress member from the anvil assembly. Another step includes moving a crush ring supported on the anvil head into engagement with the anvil cap to move the o-ring relative to the anvil head. Yet another step involves spacing the o-ring and the anvil head relative to one another in response to engagement of the crush ring with the anvil head to provide a gap between the o-ring and the anvil head sufficient to enable the extension portion of the anvil buttress member to be released from between the o-ring and the anvil head.

Other aspects, features, and advantages will be apparent from the description, drawings, and claims.

BRIEF DESCRIPTION OF DRAWINGS

The accompanying drawings, which are incorporated in and constitute a part of this specification, illustrate embodiments of the disclosure and, together with a general description of the disclosure given above and the detailed description given below, serve to explain the principles of the disclosure, wherein:

FIGS. 5-6 are progressive cross-sectional views of the anvil assembly and a distal portion of the shaft member, each view showing the anvil assembly in a different configuration.

DETAILED DESCRIPTION

Figure 1:
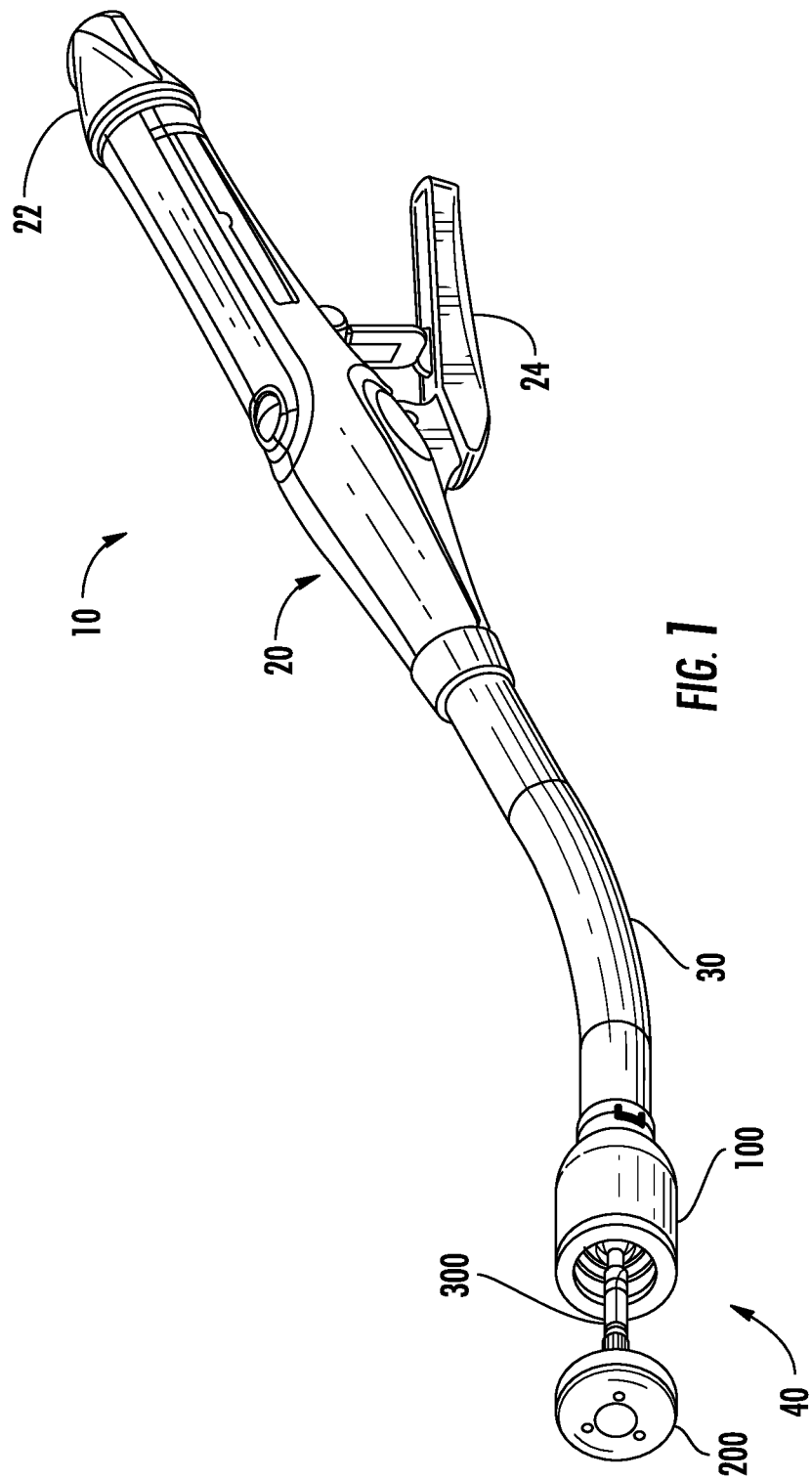
FIG. 1 is a perspective view of a circular surgical stapling device according to the present disclosure.
Figure 2:
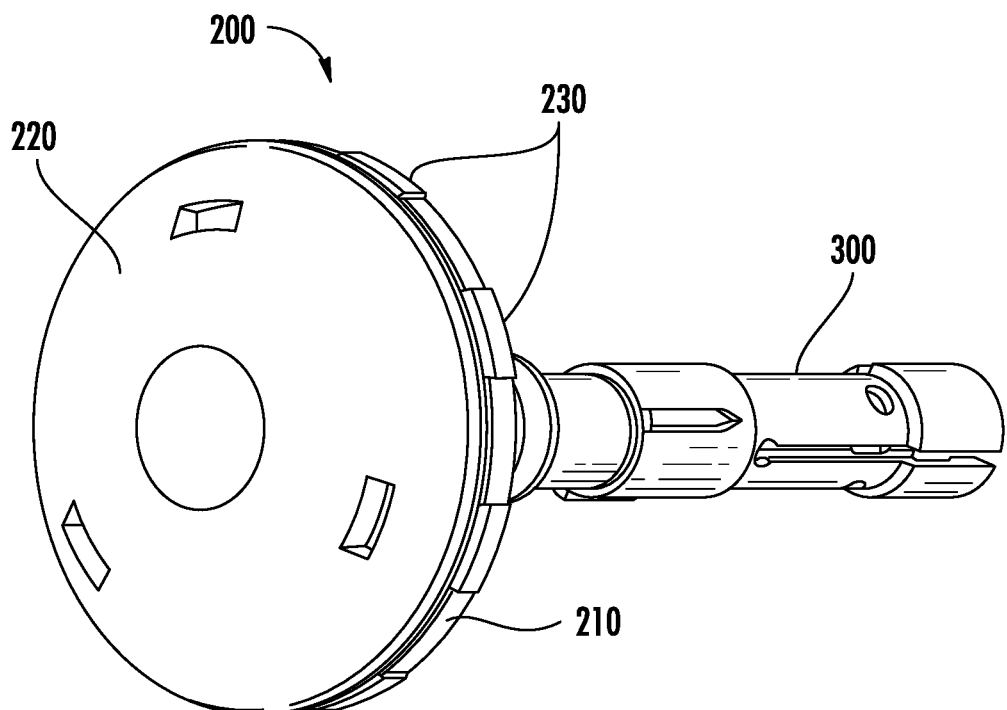
FIG. 2 is an enlarged top perspective view of an embodiment of an anvil assembly and a shaft member of the presently disclosed circular surgical stapling device.
Figure 3:
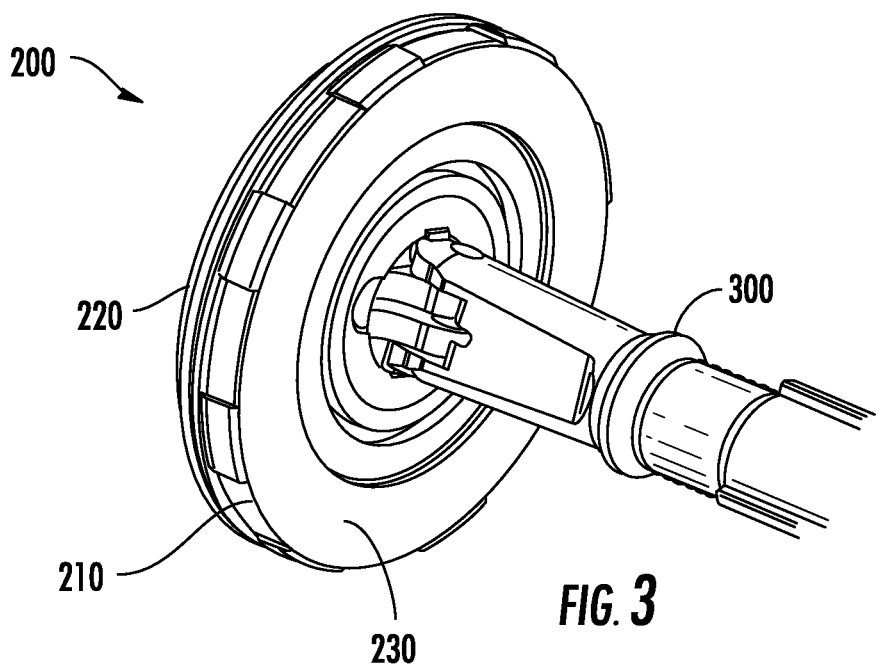
FIG. 3 is a bottom perspective view of the anvil assembly and a portion of the shaft member.

As used herein, the term "clinician" refers to a doctor, a nurse, or any other care provider and may include support personnel. Particular embodiments of the present disclosure will be described herein with reference to the accompanying drawings. As shown in the drawings and as described throughout the following description, and as is traditional when referring to relative positioning on an object, the term "proximal" refers to the end of the device that is closer to the clinician and the term "distal" refers to the end of the device that is farther from the clinician. In the following description, well-known functions or constructions are not described in detail to avoid obscuring the present disclosure in unnecessary detail.

Referring initially to FIG. 1, a circular surgical stapling device for use with a buttress material is disclosed herein and is generally designated as 10. In embodiments, the surgical stapling device 10 is adapted for reuse and, in certain embodiments, the surgical stapling device 10 is adapted for a single use and can be disposable.

The circular stapling device 10 includes a handle assembly 20, a tubular elongate body 30, and an end effector 40. The end effector 40 can be provided as a removable and replaceable assembly. The handle assembly 20 includes a rotatable advancing member 22 and a pivotable trigger member 24 that are operatively coupled to any number of drivers supported by the surgical stapling device 10 to effectuate a firing of the surgical stapling device 10. The elongate body 30 extends distally from a distal end portion of the handle assembly 20 to a proximal end portion of the end effector 40 so that the elongate body 30 is disposed between the handle assembly 20 and the end effector 40. In some embodiments, the elongate body 30 has a linear shape along the length of the elongate body 30, and in certain embodiments, the elongate body 30 has a curved shape along the length of the elongate body 30.

The end effector 40 includes a fastener cartridge assembly 100, an anvil assembly 200, and a shaft 300. The shaft 300 includes a proximal end portion that is secured to the fastener cartridge assembly 100 and a distal end portion that is secured to the anvil assembly 200. In embodiments, the fastener cartridge assembly 100 and/or the anvil assembly 200 may be replaced and the circular stapling device 10 may be reused. In embodiments, the end effector 40 supports a knife assembly with a substantially cylindrical knife 400 (FIG. 6) adapted to cut tissue.

Reference may be made to U.S. Pat. No. 5,915,616 to Viola et al. and commonly owned U.S. Patent Application Publication No. 2011/0174099, the entire contents of which are incorporated herein by reference, for a detailed discussion of the construction and operation of exemplary circular stapling devices.

Turning now to FIGS. 2-6, the anvil assembly 200 includes a circular anvil head 210, an o-ring 215, an anvil cap 220, a circular anvil buttress member 230, a crush ring member 240, an anvil plate 250, and a ring assembly 260.

Figure 4:
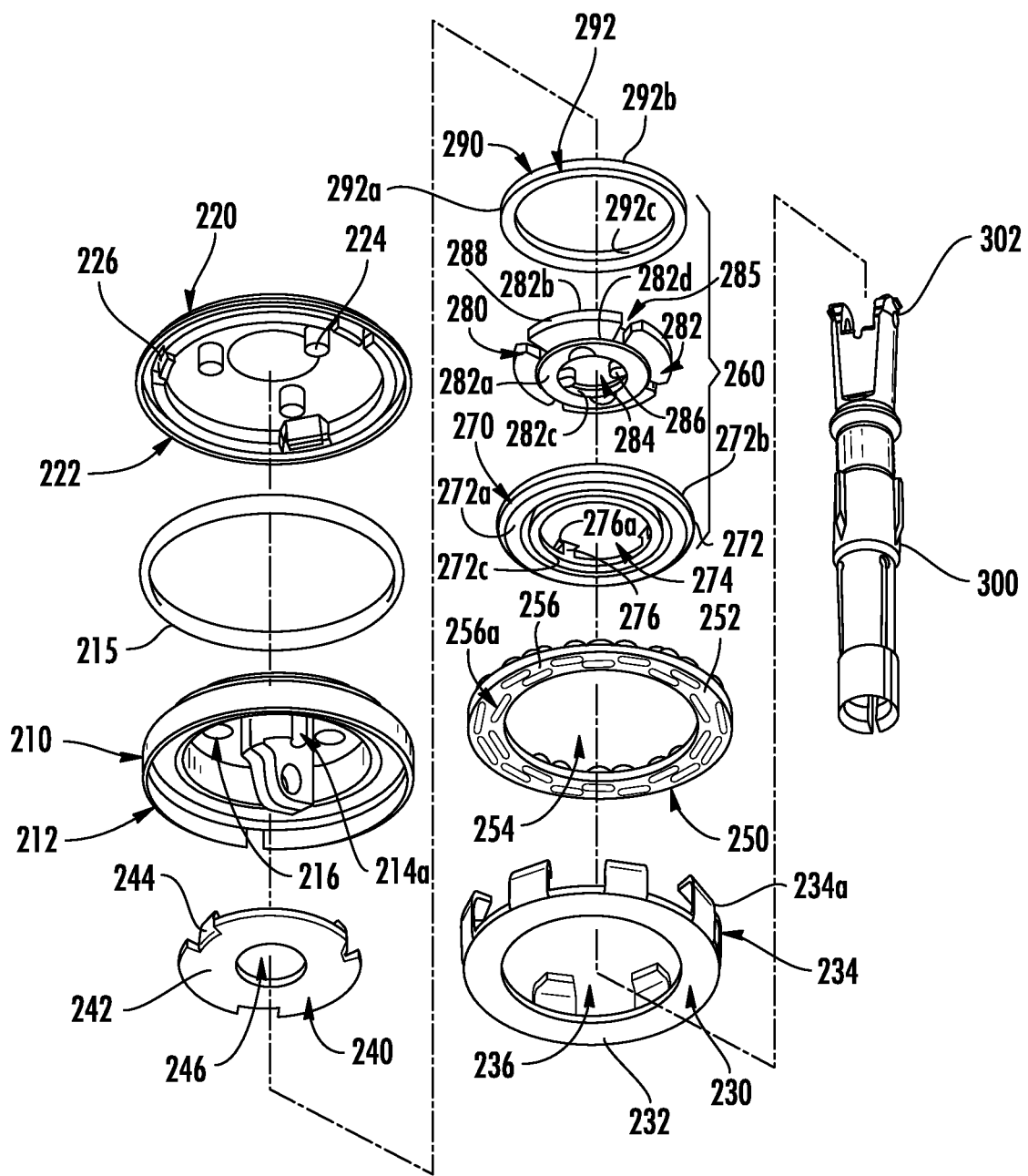
FIG. 4 is a perspective view, with parts separated, of the anvil assembly and the shaft member.

With continued reference to FIG. 4, the circular anvil head 210 includes a head body 212 that supports the crush ring member 240, the ring assembly 260, and the anvil plate 250. The head body 212 has a connector 214 that extends proximally from the head body 212 and is dimensioned to operatively couple to a distal end portion 302 of the shaft 300. The connector 214 defines a pair of opposed channels 214a. One or more engaging passages 216 are defined by the head body 212 and extend through the head body 212. As shown in FIGS. 5-6, a distal surface of the head body 212 includes one or more ramped partitions 218 that separate a first recess 218a and a second recess 218b defined on opposite sides of the ramped partition 218.

Referring again to FIG. 4, the anvil cap 220 includes a cap body 222 that is supported on the distal surface of the anvil head 210 so that the o-ring 215 is positionable between the cap body 222 and the anvil head 210. In particular, the cap body 222 defines an annular groove 222a within which the o-ring 215 is dimensioned to be received. The cap body 222 includes one or more engaging features 224 and one or more snap features 226 that extend proximally from the cap body 222. Referring also to FIGS. 5-6, the snap feature 226 includes a tooth 226a that extends radially inwardly. The first and second recesses 218a, 218b of the anvil head 210 are each dimensioned to receive the tooth 226a to facilitate securement of the anvil cap 220 to the anvil head 210. The cap body 222 defines an opening 228 dimensioned to enable the snap feature 226 to flex radially outwardly to permit the anvil cap 220 to move relative to the anvil head 210 between approximated and unapproximated positions.

The anvil plate 250 secures to the proximal surface of the anvil head 210 and has an annular body 252 that defines an opening 254 therethrough. The annular body 252 has a tissue engaging surface 256 that defines a plurality of fastener forming pockets 256a. The plurality of fastener forming pockets 256a is arranged in an annular array about the tissue engaging surface 256 of the annular body 252.

The circular anvil buttress member 230 is selectively supported on the anvil plate 250 and has an annular body portion 232 and one or more extension portions 234 that extends radially from the body portion 232. The body portion 232 is dimensioned to overly the tissue engaging surface 256 of the anvil plate 250 and defines a central opening 236 therethrough. The extension portion 234 includes a plurality of spaced apart tabs 234a that extend radially outwardly about the body portion 232. The plurality of spaced apart tabs 234a are selectively positionable between the proximal surface of the anvil cap 220 and the distal surface of the anvil head 210 to selectively secure the annular body portion 232 against the tissue engaging surface 256 of the anvil plate 250 when the anvil cap 220 is disposed in the approximated position. As described in greater detail below, the extension portion 234 is releasable from the between the anvil cap 220 and the anvil head 210 when the anvil cap 220 is moved to the unapproximated position so that the body portion 232 separates from the tissue engaging surface 256 of the anvil plate 250.

The crush ring member 240 is supported on the anvil head 210 and includes a generally annular body 242 having a plurality of tab members 244 that secure to a proximal surface of the anvil head 210 and extend from the body 242 at radially spaced locations along an outer surface of the body 242. The crush ring member 240 is dimensioned to be spaced from the one or more engaging features 224 of the cap body 222 when the anvil cap 220 is disposed in the approximated position and movable into engagement with the one or more engaging features 224 to move the anvil cap 220 to the unapproximated position. The annular body 242 defines an aperture 246 therethrough that is dimensioned to receive the connector 214 of the head body 212 when the crush ring member 240 is secured to the anvil head 210.

As illustrated in FIG. 4, the ring assembly 260 is supported between the anvil head 210 and the anvil plate 250. The ring assembly 260 includes a first annular member 270, a second annular member 280, and a third annular member 290.

The first annular member 270 includes a body 272 having a proximal surface 272a and a distal surface 272b with a central opening 274 defined by an inner surface 272c that extends between the proximal surface 272a and the distal surface 272b of the body 272. The body 272 includes a plurality of annularly spaced apart projections 276 that extend distally from the distal surface 272b of the body 272. Each projection 276 includes a pair of opposed support arms 276a that extend from the projection 276. The opposed support arms 276a are disposed substantially transverse to the projection 276.

The second annular member 280 includes a body 282 having a proximal surface 282a and a distal surface 282b with a central opening 284 defined by an inner surface 282c that extends between the proximal surface 282a and the distal surface 282b of the body 282. The body 282 includes a pair of opposed nubs 286 that extend from the inner surface 282c and are dimensioned to slide within the channels 214a defined in the connector 214 of the anvil head 210. The body 282 includes a plurality of ledges 288 extend from an outer surface 282d of the body 282 and radially about the outer surface 282d of the body 282. Adjacent ledges 288 define a passage 285 therebetween that is dimensioned to receive the projections 276 of the first annular member 270 such that the opposed support arms 276a of the projections 276 are supported against the adjacent ledges 288 on the distal surface 282b of the second annular member 280 when the first and second annular members 270, 280 are secured together. The portion of the outer surface 282d of the body 282 positioned proximally of the ledges 288 is dimensioned to be seated within the central opening 274 defined by the first annular member 270 when the first and second annular members 270, 280 are secured together. As shown in FIGS. 5 and 6, at least portions of the proximal surfaces of the first and second annular members 270, 280 are substantially aligned when the first and second annular members 270, 280 are secured together.

The third annular member 290 includes a body 292 having a proximal surface 292a and a distal surface 292b with a central opening 294 defined by an inner surface 292c that extends between the proximal surface 292a and the distal surface 292b of the body 292. As shown in FIGS. 5 and 6, when the annular members of the ring assembly 260 are secured together, the inner surface 292c of the third annular member 290 radially surrounds an outer surface of the ledges 288 of the second annular member 280 and retains the projections 276 of the first annular member 270 within the passages 285 of the second annular member 280. In this regard, the distal surface 272b of the first annular member 270 engages the proximal surface 292a of the third annular member 290 and at least portions of the distal surface 292b of the third annular member 290 and the distal surface 282b of the second annular member 280 are disposed in substantial alignment and in contact with a proximal surface of the crush ring 240.

During operation of the surgical stapling device 10, the anvil assembly 200 and the cartridge assembly 100 are approximated by the actuation of advancing member 22 until the anvil assembly 200 and the cartridge assembly 100 are suitably clamped against tissue of a patient. The trigger member 24 is then actuated to fire the surgical stapling device 10. Upon a firing of the surgical stapling device 10, the legs of the fasteners supported within the cartridge assembly 100 are advanced through the clamped tissue and any buttress material clamped against tissue including the anvil buttress member 230 and any buttress material that may supported on the cartridge assembly. As the fasteners are distally advanced, the legs of the fasteners are formed by the fastener forming pockets 256a defined in the anvil plate 250 to secure the buttress material including the anvil buttress member 230 to the tissue.

Referring again to FIGS. 5-6, the knife 400 is simultaneously or thereafter advanced into the anvil assembly 200 to sever the clamped tissue and to advance into engagement with the proximal surface 272a of the first annular member 270 of the ring assembly 260. Upon engagement with the first annular member 270, the knife 400 distally drives the entire ring assembly 260 toward the anvil cap 220. Notably, as the ring assembly 260 is moved distally, the pair of opposed nubs 286 of the second annular member 280 slide through the channels 214a of anvil head 210 such that the ring assembly 260 drives the crush ring member 240 distally into engagement with the one or more engaging features 224 of the anvil cap 220.

The distal movement of the crush ring member 240 into engagement with the one or more engaging features 224 of the anvil cap 220 separates the proximal surface of the cap body 222 of the anvil cap 220 from the distal surface of the head body 212 of the anvil head 210 so that the o-ring 215 separates from the extension portions 234 of the anvil buttress member 230. In particular, the teeth 226a of the snap features 226 cam against the ramped partitions 218 so that each snap feature 226 flexes radially outwardly into the opening 228 of the cap body 222 from the first recess 218a of the head body 212 to enable the anvil cap 220 to separate from the anvil head 210 as the anvil cap 220 moves from the approximated position to the unapproximated position. After camming over the ramped partitions 218, the teeth 226a of the snap features 226 snap or flexes radially inwardly into the second recess 218b of the head body 212 to maintain the anvil cap 220 secured to the anvil head 210. The separation of the cap body 222 and the head body 212 creates a space or gap "G" between the proximal surface of the cap body 222 and a distal surface of the head body 212 to free the extension portion 234 of the anvil buttress member 230 from between the anvil head 210 and the o-ring 215 so that the anvil buttress member 230 is secured to the tissue independent of the surgical stapling device 10.

Figure 7:
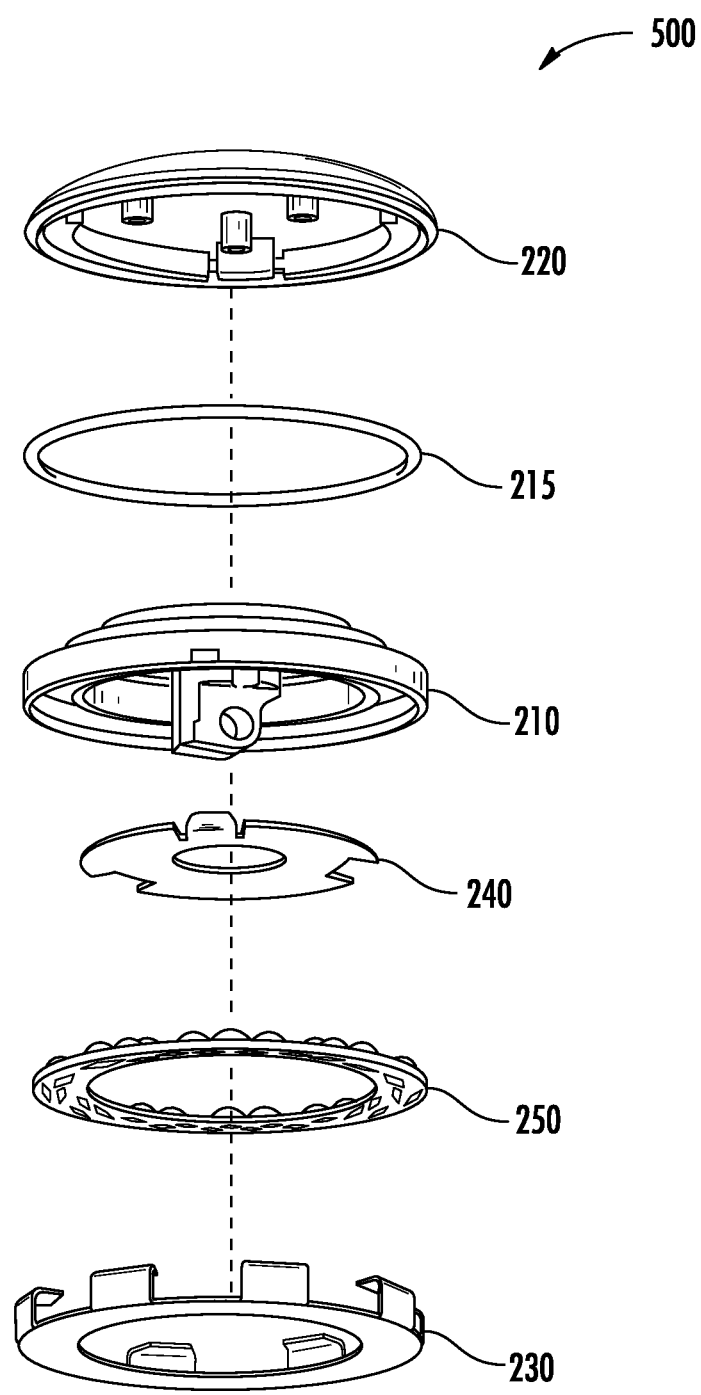
FIG. 7 is a perspective view, with parts separated, of another embodiment of an anvil assembly.

As illustrated in FIG. 7, an embodiment of an anvil assembly is generally referred to as anvil assembly 500 and is substantially similar to anvil assembly 200 and thus, anvil assembly 500 is described herein only to the extent necessary to describe the differences in construction and operation of the anvil assembly 500. Anvil assembly 500 includes a circular anvil head 210, an o-ring 215, an anvil cap 220, a circular anvil buttress member 230, a crush ring member 240, and an anvil plate 250. Notably, anvil assembly 500 does not include ring assembly 260 and thus, when the circular knife 400 is advanced into the anvil assembly 500 during operation, the blade of the circular knife 400 directly engages the proximal surface of crush ring member 240 to drive the crush ring member 240 distally into engagement with the anvil cap 220. In particular, as noted above, the distal movement of the crush ring member 240 into engagement with the one or more engaging features 224 of the anvil cap 220 separates the proximal surface of the cap body 222 of the anvil cap 220 from the distal surface of the head body 212 of the anvil head 210 so that the o-ring 215 separates from the extension portions 234 of the anvil buttress member 230 to free the anvil buttress member 230.

Although a manually operated handle assembly is shown in FIG. 1, in any of the embodiments disclosed herein, the handle assembly can be powered by a motor and an external or internal power source. One or more drive shafts extending through the elongate body can drive the various functions (i.e., approximation, stapling and cutting) of the instrument.

In any of the embodiments disclosed herein, one or more of the crush ring 240 and parts of the ring assembly 260 could be eliminated. Furthermore, the circular knife may directly move the anvil cap 220 above to release the buttress member.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Indeed, any combination of any of the presently disclosed elements and features is within the scope of the present disclosure. Accordingly, the subject matter of the present disclosure is not to be limited by what has been particularly shown and described.

What is claimed is:

1. An anvil assembly comprising:
   an anvil head defining a first recess and a second recess, the first recess and the second recess separated by a ramped partition;
   a buttress member supported on the anvil head;
   an anvil cap movable relative to the anvil head between an approximated position and an unapproximated position, the anvil cap including a snap feature, the snap feature being positionable within the first recess when the anvil cap is disposed in the approximated position and being positionable within the second recess when the anvil cap is disposed in the unapproximated position, the snap feature configured to cam over the ramped feature as the anvil cap moves from the approximated position to the unapproximated position, the snap feature configured to flex outwardly from the first recess as the snap feature cams over the ramped partition and configured to flex inwardly into the second recess after camming over the ramped partition, the snap feature configured to maintain the anvil cap secured to the anvil head when the snap feature is disposed in the second recess; and a crush member movable into engagement with the anvil cap to move the anvil cap toward the unapproximated position so that the buttress member releases from the anvil head.

2. The anvil assembly of claim 1, wherein the anvil cap supports an o-ring.

3. The anvil assembly of claim 2, wherein the o-ring is formed of an elastomeric material.

4. The anvil assembly of claim 2, wherein the o-ring is disposed in a compressed condition when the anvil cap is disposed in the approximated position, and wherein the o-ring is disposed in an uncompressed condition when the anvil cap is disposed in the unapproximated position.

5. The anvil assembly of claim 2, wherein the buttress member includes a body portion and an extension portion that extends from the body portion.

6. The anvil assembly of claim 2, wherein the anvil cap defines a groove configured to support the o-ring.

7. The anvil assembly of claim 6, wherein the groove is defined in a bottom surface of the anvil cap.

8. The anvil assembly of claim 5, wherein the extension portion includes at least one tab, the o-ring being compressed against the at least one tab when the anvil cap is disposed in the approximate position to maintain the body portion of the buttress member supported on a tissue engaging surface of the anvil head.

9. A stapling device, comprising:
a handle assembly;
an elongate body that extends from the handle assembly; and
an end effector mounted on a distal end of the elongate body and including a cartridge assembly and an anvil assembly, the anvil assembly including:
an anvil head defining a first recess and a second recess separated by a ramped partition;
a buttress member supported on the anvil head;
an anvil cap movable relative to the anvil head between an approximated position and an unapproximated position, the anvil cap including a snap feature configured to cam over the ramped feature as the anvil cap moves from the approximated position to the unapproximated position, the snap feature configured to flex outwardly from the first recess as the snap feature cams over the ramped partition and configured to flex inwardly into the second recess after camming over the ramped partition, the snap feature configured to maintain the anvil cap secured to the anvil head when the snap feature is disposed in the second recess; and
a crush member movable into engagement with the anvil cap to move the anvil cap toward the unapproximated position so that the buttress member releases from the anvil head.

10. The stapling device of claim 9, wherein the anvil cap supports an o-ring.

11. The stapling device of claim 10, wherein the o-ring is formed of an elastomeric material.

12. The stapling device of claim 10, wherein the o-ring is disposed in a compressed condition when the anvil cap is disposed in the approximated position, and wherein the o-ring is disposed in an uncompressed condition when the anvil cap is disposed in the unapproximated position.

13. The stapling device of claim 9, wherein the buttress member includes a body portion and an extension portion that extends from the body portion.

14. The stapling device of claim 9, wherein, the snap feature is positionable within the first recess when the anvil cap is disposed in the approximated position and wherein the snap feature is positionable within the second recess when the anvil cap is disposed in the unapproximated position.

15. The stapling device of claim 10, wherein the anvil cap defines a groove configured to support the o-ring.

16. The stapling device of claim 15, wherein the groove is defined in a bottom surface of the anvil cap.

17. A circular stapling device, comprising:
a handle assembly;
an elongate body that extends from the handle assembly; and
an end effector mounted on a distal end of the elongate body and including a cartridge assembly and an anvil assembly, the anvil assembly including:
an anvil head defining a first recess and a second recess separated by a ramped partition;
a buttress member supported on the anvil head;
an anvil cap movable relative to the anvil head between an approximated position and an unapproximated position, the anvil cap including a snap feature configured to cam over the ramped feature as the anvil cap moves from the approximated position to the unapproximated position, the snap feature configured to flex from the first recess as the snap feature cams over the ramped partition and into the second recess to maintain the anvil cap secured to the anvil head; and
a crush ring movable into engagement with the anvil cap to move the anvil cap toward the unapproximated position so that the buttress member releases from the anvil head.

* * * * *